United States Patent
Atala

(10) Patent No.: US 7,811,332 B2
(45) Date of Patent: Oct. 12, 2010

(54) RECONSTRUCTION METHOD FOR UROLOGICAL STRUCTURES UTILIZING POLYMERIC MATRICES

(75) Inventor: Anthony Atala, Winston Salem, NC (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 11/187,702

(22) Filed: Jul. 22, 2005

(65) Prior Publication Data

US 2006/0002972 A1    Jan. 5, 2006

Related U.S. Application Data

(63) Continuation of application No. 10/361,950, filed on Feb. 10, 2003, now abandoned, which is a continuation of application No. 09/111,210, filed on Jul. 7, 1998, now abandoned, which is a continuation of application No. 08/291,287, filed on Aug. 16, 1994, now abandoned.

(51) Int. Cl.
*A61F 2/04*   (2006.01)

(52) U.S. Cl. .............. 623/23.64; 623/23.65; 623/23.66; 600/37; 424/423

(58) Field of Classification Search ................ 600/37; 606/151, 154, 155–156; 623/23.64, 23.65, 623/23.66, 23.71, 11.11
See application file for complete search history.

(56) References Cited

U.S. PATENT DOCUMENTS

| | | | |
|---|---|---|---|
| 3,463,158 A * | 8/1969 | Schmitt et al. ............. 606/154 |
| 4,182,339 A | 1/1980 | Hardy, Jr. |
| 4,199,864 A * | 4/1980 | Ashman ..................... 433/175 |
| 4,255,820 A * | 3/1981 | Rothermel et al. ........ 623/13.11 |
| 4,286,341 A * | 9/1981 | Greer et al. ................. 623/1.4 |
| 4,400,833 A * | 8/1983 | Kurland ................... 623/13.17 |
| 4,458,678 A | 7/1984 | Yannas |
| 4,502,159 A * | 3/1985 | Woodroof et al. ......... 623/1.41 |
| 4,520,821 A | 6/1985 | Schmidt et al. |
| 4,536,158 A * | 8/1985 | Bruins et al. ............. 433/201.1 |
| 4,594,407 A | 6/1986 | Nyilas |
| 4,693,721 A * | 9/1987 | Ducheyne ................ 623/23.54 |
| 4,769,037 A | 9/1988 | Midcalf |
| 4,770,664 A * | 9/1988 | Gogolewski ............... 427/2.24 |
| 4,841,962 A * | 6/1989 | Berg et al. ................... 602/50 |
| 4,883,618 A * | 11/1989 | Barrows ...................... 264/49 |
| 4,963,489 A | 10/1990 | Naughton |
| 4,996,154 A | 2/1991 | Gabriels, Jr. |
| 5,007,934 A * | 4/1991 | Stone ...................... 623/14.12 |
| 5,032,508 A | 7/1991 | Naughton |
| 5,085,629 A | 2/1992 | Goldberg et al. |
| 5,160,490 A | 11/1992 | Naughton |
| 5,163,958 A * | 11/1992 | Pinchuk .................... 623/23.49 |
| 5,224,953 A | 7/1993 | Morgentaler |
| 5,261,898 A | 11/1993 | Polin et al. |
| 5,376,376 A | 12/1994 | Li |
| 5,433,996 A | 7/1995 | Kranzler et al. |
| 5,480,436 A | 1/1996 | Bakker et al. |
| 5,762,966 A | 6/1998 | Knapp, Jr. et al. |
| 5,766,618 A | 6/1998 | Laurencin et al. |
| 5,804,178 A | 9/1998 | Vacanti et al. |
| 5,830,493 A * | 11/1998 | Yokota et al. ............... 424/426 |
| 5,947,893 A | 9/1999 | Argawal et al. |
| 6,309,635 B1 * | 10/2001 | Ingber et al. ............... 424/93.7 |
| 7,371,403 B2 * | 5/2008 | McCarthy et al. ........... 424/445 |
| 7,569,076 B2 * | 8/2009 | Atala ....................... 623/23.65 |
| 2002/0052649 A1 * | 5/2002 | Greenhalgh ................ 623/1.35 |
| 2002/0150604 A1 | 10/2002 | Yi et al. |
| 2006/0002972 A1 * | 1/2006 | Atala ......................... 424/423 |

FOREIGN PATENT DOCUMENTS

| | | | |
|---|---|---|---|
| EP | 0194192 | | 9/1986 |
| GB | 2011274 | | 7/1979 |
| JP | 2008220388 A | * | 9/2008 |
| SU | 1034717 | | 8/1983 |
| WO | 89/01967 A1 | | 3/1989 |
| WO | 90/02796 A1 | | 3/1990 |

(Continued)

OTHER PUBLICATIONS

Atala, A., et al., Formation of urothelial structures in vivo from dissociated cells attaches to biological polymer scaffolds in vivo, *J. Urol. Part 1*, 148 :658 (1992).

(Continued)

*Primary Examiner*—Paul Prebilic
(74) *Attorney, Agent, or Firm*—Nixon Peabody LLP

(57) ABSTRACT

A method for repairing defects and reconstructing urological structures in vivo has been developed using a fibrous, open, synthetic, biodegradable polymeric matrix which is configured to provide the desired corrective structure. The matrix is shaped to correct the defect, then implanted surgically to form a scaffolding for the patient's own cells to grow onto and into. The implantation of the matrix initiates an inflammatory reaction, resulting in urothelial cells, endothelial cells and mesenchymal cells migrating into the matrix. The polymer forming the matrix is selected to be biocompatible and degradable in a controlled manner over a period of one to six months, in the preferred embodiment. A preferred material is a poly(lactic acid-glycolic acid) in a fibrous form, such as a woven or non-woven mesh. Examples demonstrate the repair of defects in bladder and urethra in rabbits and defects in ureter in dogs.

7 Claims, No Drawings

FOREIGN PATENT DOCUMENTS

| WO | 90/12604 A1 | 11/1990 |
|----|-------------|---------|
| WO | 92/15259 A1 | 9/1992 |
| WO | 93/07913 A1 | 4/1993 |

OTHER PUBLICATIONS

Atala, A., et al., "Pediatric urology—future perspectives," In: *Clinical Urology*, edited by R.J. Krane, M.B. Siroky and J.M. Fitzpatrick (Philadelphia: J.B. Lippincott) (1993).

Burke, et al., "Successful use of a physiologically acceptable artificial skin in the treatment of an extensive burn injury," *Ann. Surg.*, 194:413 (1981).

Chlapowski, F.J., Long term growth and maintenance of stratified rat urothelium in vitro,: *Cell Tissue Kinet*, 22:245-257 (1990).

Cima, et al., "Hepatocyte culture on biodegradable polymeric substrates," *Biotechnol. Bioeng.* 38:145 (1991).

Craig, P.H., et al., "A biological comparison of polyglactin 910 and polyglycolic acid synthetic absorbable sutures,"*Surg.* 141:1010 (1975).

Freeman, M.R., et al., "Induction and segregation of glial intermediate filament expression in the RT4 family of peripheral nervous system cell lines," *Proc. Natl. Acad. Sci. USA* 84:5808 (1987).

Green, et al., Growth of cultured human epidermal cells into multiple epithelia suitable for grafting, *Proc. Natl. Acad. Sci*. 76:5665 (1979).

Hendren, W.H., et al., "Bladder mucosa graft for construction of the male urethra," *J. Pediatr. Surg.* 21:189-192 (1986).

Langer, R. et al., "Biocompatible controlled release polymers for delivery of polypeptides and growth factors," *J. Cell Biochem.* 45:340-345 (1991).

Laemmil, U.K., "Cleavage of structural proteins during assembly of the head of bacteriophage T4," *Nature* (London) 227:680-685 (1970).

O'Connor, et al., "Grafting of burns with culture epithelium prepared from autologous epidermal cells," *Lancet* 1:75 (1981).

Ransley, P.G., et al., << Autologous bladder mucosa graft for urethral substitution,>> Br. J. Urol. 58:331-333 (1986).

Reznikoff, C.A. et al., "Growth kinetics and differentiation in vitro of normal human uroepithelial cells on collagen gel substrates in defined medium," *J. Cell Physiol*. 131:285-301 (1987).

Romagnoli, G., et al. "Treatment of posterior hypospadias by the autologous graft of cultures urethral epithelium," New England J. Med., 323:537-530 (1990).

Tachibana, et al., "Ureteral Replacement Using Collagen Sponge Tube Grafts," *J. of Urol*. 133:866-869 (1985).

Thuroff, et al., "Cultured Rabbit Vesical Smooth Muscle Cells for Lining of Dissolvable Synthetic Prosthesis," *Urology* XXI:155-158 (1983).

Tseng, S.C.G., et al., "Correlation of specific kerritans with differentiation: monoclonal antibody studies," *Cell* 30:361-372 (1982).

Vacanti, "Beyond Transplantation," *Arch. Surg* 123:545 (1988).

Vacanti, et al. "Selective cell transplantation using bioabsorbable artificial polymers as matrices," J. Ped. Surg. 23:3 (1988).

Vacanti, et al., "Synthetic polymers seeded with chondrocytes provide a template for new cartilage formation,"*J. Plast. Reconstr. Surg.* 88:753 (1991).

Van Der Kwast, et al., "Establishment and characterization of long-term primary mouse urothelial cell cultures," *Urol. Res*. 17:289-293 (1989).

Thuroff, et al., "Cultured Rabbit Vesical Smooth Muscle Cells for Lining of Dissolvable Synthetic Prosthesis," Urology XXI:155-158 (1983).

Tseng, S.C.G., et al., "Correlation of specific kerritans with different types of epithelial differentiation: monoclonal antibody studies," Cell 30:361-372 (1982).

Uyama, S. et al., "Delivery of Whole Liver-equivalent Hepatocyte Mass Using Polymer Devices and Hepatotrophic Stimulation," Transplantation, vol. 55, No. 4, 932-5 (Apr. 1993).

Vacanti, "Beyond Transplantation," Arch. Surg. 123:545 (1988).

Vacanti, et al., "Synthetic polymers seeded with chondrocytes provide a template for new cartilage formation," J. Plast. Reconstr. Surg. 88:753 (1991).

Van Der Kwast, T.H. et al., "Establishment and characterization of long terim primary mouse urothelial cell cultures," Urol. Res. 17:289-293 (1989).

Walton, R. and Brown, R., "Tissue Engineering of Biomaterials for Composite Reconstruction: An Experimental Model," Annals of Plastic Surgery, vol. 30, No. 2, 105-10 (Feb. 1993).

Ashkar, S. et al., "Regulation of Gluconeogenesis in Swine Kidney Proximal Tubule Cells," Molecular and Cellular Biochemistry, 87:105-118 (1989).

Atala, A., et al., "Pediatric urology—future perspectives," In: Clinical Urology, edited by R. J. Krane M.B. Siroky and J. M. Fitzpatrick (Philadelphia: J.B. Lippincott, 1994), pp. 507-524.

Atala, A. et al. "Implantation in vivo and retrieval of artificial structures consisting of rabbit and human urothelium and human bladder muscle," The Journal of Urology, 1993, vol. 150, 608-612.

Atala, A. et al. "Injectable Alginate Seeded with Chondrocytes as Potential Treatment for Vesicoureteral Reflux," The Journal of Urology, vol. 150, 745-7 (Aug. 1993).

Bazeed, et al., "New treatment for urothelial structures," Urology 21:53-57 (1983).

Ben-Ze'ev, A. et al., "Cell-cell and Cell-matrix Interactions Differentially Regulate the Expression of Hepatic and Cytoskeletal Genes in Primary Cultures of Rat Hepatocytes," PNAS, vol. 85, 2161-5 (Apr. 1988).

Bissell, D. et al., "Interactions of Rat Hepatocytes with Type IV Collagen, Fibronectin and Laminin Matrices. Distinct Matrix-controlled Modes of Attachment and Spreading," European Journal of Cell Biology, vol. 40, 72-8 (1986).

Boogaard, P.J. et al., "Renal Proximal Tubular Cells in Suspension or in Primary Culture as In Vitro Models to Study Nephrotoxicity," (ABST) Chem. Biol. Interact, 76(3):251-291 (1990).

Burke, J., "The Effects of the Configuration of an Artificial Extracellular Matrix on the Development of a Functional Dermis," The Role of Extracellular Matrix in Development, Alan R. Liss, Inc., eds (NY), 351-55 (1984).

Burke, et al., "Successful use of physiologically acceptable artificial skin in the treatment of an extensive burn injury," Ann. Surg., 194:413 (1981).

Chlapowski, F.J., "Long-term growth and maintenance of stratified rat urothelium in vitro," Cell Tissue Kinet. 22:245-257 (1989).

Cilento, B. et al., "Phenotypic and Cytogenetic Characterization of Human Bladder Urothelia Expanded in Vitro" J. Urol., vol. 152: 665-670 (Aug. 1994).

Cima, et al., "Hepatocyte culture on biodegradable polymeric substrates," Biotechnol. Bioeng. 38.145 (1991).

Craig, P.H., et al., "A biological comparison of polyglactin 910 and polyglycolic acid synthetic absorbable sutures," Surg. 141:1-10 (1975).

Culliton, B., "Gore Tex Organoids and Genetic Drugs," Science, vol. 246, 747-9 (Nov. 10, 1989).

Davis, G. et al., "Human Amnion Membrane Serves as a Substratum for Growing Axons in Vitro and in Vivo" Science, vol. 236, 1106-9 (May 29, 1987).

Ebata, H. et al., "Liver Regeneration Utilizing Isolated Hepatocytes Transplanted into the Rat Spleen," Surg Forum, vol. 29, 338-40 (1978).

Fontaine, M. et al., "Transplantation of Genetically Altered Hepatocytes Using Cell-Polymer Constructs," Transplantation Proceedings, vol. 25, No. 1, 1002-4 (Feb. 1993).

Freeman, M.R., et al., "Induction and segregation of glial intermediate filament expression in the RT4 family of peripheral nervous system cell lines," Proc. Natl. Acad. Sci. USA 84.5808 (1987).

Gilbert, J. et al., "Cell Transplantation of Genetically Altered Cells on Biodegradable Polymer Scaffolds in Syngeneic Rats," Transplantation, vol. 56, No. 2, 423-7 (Aug. 1993).

Green, et al., "Growth of cultured human epidermal cells into multiple epithelia suitable for grafting," Proc. Natl. Acad. Sci. 76:5665 (1979).

Hendren, W.H. et al., "Bladder mucosa graft for construction of the male urethra," J. Pediatr. Surg. 21:189-192 (1986).

Henry, E.W. et al., "Nerve Regeneration Through Biodegradable Polyester Tubes," Experimental Neurology, vol. 90, 652-76 (1985).

Humes, H. D., et al., "Effects of Transforming Growth Factor-β, Transforming Growth Factor-α, and Other Growth Factors on Renal Proximal Tubule Cells," Laboratory Investigation, 64(4): 538-545 (1991).

Ingber, D. et al., "Endothelial Growth Factors and Extracellular Matrix Regulate DNA Synthesis Through Modulation of Cell and Nuclear Expansion," In Vitro Cellular * Developmental Biology, vol. 23, No. 5, 387-94 (May 1987).

Jauregui, H.O. et al., "Attachment and Long Term Survival of Adult Rat Hepatocytes in Primary Monolayer Cultures: Comparison of Different Substrata and Tissue Culture Media Formulations," In Vitro Cellular & Developmental Biology, vol. 22, No. 1, 13-22 (Jan. 1986).

Laemmli, U.K., "Cleavage of structural proteins during assembly of the head of bacteriophage T4," Nature (London) 227:680-685 (1970).

Michalopoulos, g. and Pitot, H.C., "Primary Culture of Parenchymal Liver Cells on Collagen Membranes," Experimental Cell Research, vol. 94, 70-8 (1975).

Mooney, D. and Vacanti, J., "Tissue Engineering Using Cells and Synthetic Polymers," Transplantation Reviews, vol. 7, No. 3, 153-62 (Jul. 1993).

Naughton, B. et al., "Long-term Growth of Rat Bone Marrow Cells in a Three-dimensional Matrix," The Anatomical Record, vol. 218, 97A (1987).

Puelacher, W.C. et al., "Tissue-engineered Growth of Cartilage: The Effect of Varying the Concentration of Chondrocytes Seeded Onto Synthetic Polymer Matrices," Int. J. Oral Maxilofac. Surge., vol. 23, 49-53 (1994).

Ransley, P.G., et al., "Autologous bladder mucosa graft for urethral substitution," Br. J. Urol. 58:331-333 (1986).

Reid, L. et al., "Long-term Cultures of Normal Rat Hepatocytes on Liver Biomatrix," Annals New York Academy of Sciences, 70-6 (1980).

Reznikoff, C.A. et al., "Growth kinetics and differentiation in vitro of normal human uroepithelial cells on collagen gel substrates in defined medium," J. Cell Physiol. 131:285-301 (1987).

Rhine, W. et al., "Polymers for sustained Macromolecule Release: Procedures to Fabricate Reproducible Delivery Systems and Control Release Kinetics," Journal of Pharmaceutical Sciences, vol. 69, No. 3, 265-70 (Mar. 1980).

Romagnoli, G., et al., "Treatment of posterior hypospadias by the autologous graft of cultures urethral epithelium," New England J. Med. 323:527-530 (1990).

Rosen, H.B. et al., "bioerodible Polyanhydrides for Controlled Drug Delivery," Biomaterials, vol. 4, 131-3 (Apr. 1983).

Sawada, N. et al., "Effects of Extracellular Matrix Components on the Grwoth and Differentiation of Cultured Rat Hepatocytes," In Vitro Cellular& Developmental Biology, vol. 23, No. 4, 267-73 (Apr. 1987).

Seckel, B.R. et al., "Nerve Regeneration Trhough synthetic Biodegradable Nerve Guides: Regulation by the Target Organ," Plastic and Reconstructive Surgery, vol. 74, No. 2, 173-81 (Aug. 1984).

Shine, H.D. et al., "Cultured Peripheral Nervous system Cells Support Peripheral Nerve Regenerations Through Tubes in the Absence of Distal Nerve Stump," Journal of Neuroscience Research, vol. 14, 393-401 (1985).

da Silva, C. et al., "an In Vivo Model to Quantify Motor and Sensory Peripheral Nerve Regeneration Using Bioresorbable Nerve Guide Tubes," Brain Research, vol. 342, 307-15 (1985).

Tachibana, M. et al., "Ureteral Replacement Using Collagen Sponge Tube Grafts," the Journal of Urology, vol. 133, 866-9 (May 1985).

Taub, M., et al., "Epidermal Growth Factor or Transforming Growth Factor α is Required for Kidney tubulogenesis in Matrigel Cultures in Serum-free Medium," Proc. Natl. Acad. Sci., 87:4002-6 (May 1990).

Thompson, J. et al., "Heparin-binding Grwoth Factor 1 Induces the Formation of Organoid Neovascular Structures in vivo" PNAS, vol. 86, 7928-32 (Oct. 1989).

Thompson, J. et al., "Implantable Bioreactors: Modem Concepts of Gene Therapy," Current Communications in Molecular Biology: Therapeutic Peptides and Proteins, Cold Spring Harbor Laboratory, eds., 143-7 (1989).

* cited by examiner

RECONSTRUCTION METHOD FOR UROLOGICAL STRUCTURES UTILIZING POLYMERIC MATRICES

CROSS-REFERENCE

This application is a Continuation of U.S. application Ser. No. 10/361,950, filed Feb. 10, 2003, abandoned, which is a Continuation of U.S. application Ser. No. 09/111,210, filed Jul. 7, 1998, abandoned, which is a Continuation of U.S. application Ser. No. 08/291,287, filed Aug. 16, 1994, abandoned.

BACKGROUND OF THE INVENTION

The present invention is generally in the area of methods for reconstruction of urothelial structures, especially bladders.

Traditionally, defects in the bladder and other urothelial structures have been corrected surgically. This has obvious disadvantages when there is a defect in the structure which requires closure of an opening for which there is insufficient tissue or when the structure itself is deformed or too small to meet the needs of the patient.

Bowel segments have been used in reconstruction of genitourinary structures in these circumstance. The use of bowel in genitourinary reconstruction is associated with a variety of complications, including metabolic abnormalities, infection, perforation, urolithiasis, increased mucus production and malignancy, as reviewed by Atala, A. and Retik, A.: Pediatric urology—future perspectives. In: Clinical Urology. Edited by R/J. Krane, M. B. Siroky and J. M. Fitzpatrick. (Philadelphia: J. B. Lippincott, 1993). Alternative approaches need to be developed to overcome the problems associated with the incorporation of intestinal segments into the urinary tract. Natural tissues and synthetic materials that have been tried previously in experimental and clinical settings include omentum, peritoneum, seromuscular grafts, de-epithelialized segments of bowel, polyvinyl sponge and polytetrafluoroethylene (Teflon). These attempts have usually failed.

It is evident that urothelial-to-urothelial anastomoses are preferable functionally. However, the limited amount of autologous urothelial tissue for reconstruction generally precludes this option. In cell transplantation, donor tissue is dissociated into individual cells or small tissue fragments and either implanted directly into the autologous host or attached to a support matrix, expanded in culture and reimplanted after expansion. Autologous skin cells have been used in this fashion in the treatment of extensive burn wounds, as reported by Green, et al., "Growth of cultured human epidermal cells into multiple epithelia suitable for grafting", *Proc. Natl. Acad. Sci.*, 76:5665 (1979); O'Connor, et al., "Grafting of burns with culture epithelium prepared from autologous epidermal cells", *Lancet*, 1:75 (1981); and Burke, et al., "Successful use of a physiologically acceptable artificial skin in the treatment of an extensive burn injury", *Ann. Surg.*, 194:413 (1981).

A suitable material for a cell transplantation matrix must be biocompatible to preclude migration and immunological complications, and should be able to support extensive cell growth and differentiated cell function. It must also be resorbable, allowing for a completely natural tissue replacement. The matrix should be configurable into a variety of shapes and should have sufficient strength to prevent collapse upon implantation. Recent studies indicate that the biodegradable polyester polymers made of polyglycolic acid seem to fulfill all of these criteria, as described by Vacanti, et al., "Selective cell transplantation using bioabsorbable artificial polymers as matrices", *J. Ped. Surg.*, 23:3 (1988); Cima, et al., "Hepatocyte culture on biodegradable polymeric substrates", *Biotechnol. Bioeng.*, 38:145 (1991); Vacanti, et al., "Synthetic polymers seeded with chondrocytes provide a template for new cartilage formation", *J. Plast. Reconstr. Surg.*, 88:753 (1991).

The feasibility of using biodegradable polymers as delivery vehicles for urothelial cell transplantation has been demonstrated by studies showing that urothelial cells will adhere to synthetic polymers composed of polyglycolic acid and survive in vivo, as reported by Atala, et al., "Formation of urothelial structures in vivo from dissociated cells attached to biodegradable polymer scaffolds in viva", *J. Urol.*, part 1, 148:658 (1992).

For implantation of cells on polymer matrices to be successful in patients, a source of an effective concentration of cells has to be available, and the urothelial cell population has to survive for extended times on implanted polymers and proliferate extensively in vivo. Most importantly, implanted cells have to remain intact as defined structures as the polymer implant degrades over time under physiological conditions. Polymer scaffolds would have to include bladder smooth muscle in concert with urothelial cells to reconstitute a functional bladder wall.

An easier solution would be to develop a method for correcting defects which did not require obtaining and implanting cells on the polymer matrices. However, initial studies with chondrocytes implanted in tissue in the absence of a matrix and implantation of polymer alone has not been demonstrated to result in appropriate ingrowth and proliferation of cells.

It is therefore an object of the present invention to provide a method and means for reconstructing defects in organ structures, especially urothelial structures such as the bladder, ureter and urethra, which does not require exogenous cells.

SUMMARY OF THE INVENTION

A method for repairing defects and reconstructing urological structures in vivo has been developed using a fibrous, open, synthetic, biodegradable polymeric matrix. The matrix is shaped to correct the defect, then implanted surgically to form a scaffolding for the patients own cells to grow onto and into. The implantation of the matrix initiates an inflammatory reaction, resulting in urothelial cells, including both endothelial cells and mesenchymal cells, migrating into the matrix. The polymer forming the matrix is selected to be biocompatible and degradable in a controlled manner over a period of one to six months in the preferred embodiment. A preferred material is a polyhydroxy acid, poly(lactic acid-glycolic acid), in a fibrous form, such as a woven or non-woven mesh.

Examples demonstrate the repair of defects in bladders in rabbits.

DETAILED DESCRIPTION OF THE INVENTION

Previous studies have indicated that cells implanted in the absence of a matrix and that matrices implanted in the absence of seeded cells do not form structures. In contrast, previous studies have indicated that very small repairs can be achieved by covering the defect with a "patch" or other biodegradable or non-degradable mesh, so that the surrounding tissue grows over the defect. The usefulness of polymeric matrices, in the absence of seeded cells, either before or after implantation of the matrix, to form tissue structures, is surprising. Based on the previous studies, one would have expected problems, including compression of the matrix after surgical attachment which would prevent cells from entering into and proliferating in the matrix to form tissue; migration into and proliferation within the matrix of the wrong cell populations; and/or that the matrix would have detached or degraded prior to tissue formation. As demonstrated by the following examples, none of these problems occurred and the materials did form tissue that effectively repaired the defects in bladders.

Polymeric Materials

A variety of polymeric materials can be used to make the matrix. In the preferred embodiment, the material is biocompatible, biodegradable over a period of one to six months, synthetic, and easily fabricated. The most preferred material is poly(lactic acid-glycolic acid).

In the preferred embodiment, the matrix is formed of a bioabsorbable, or biodegradable, synthetic polymer such as a polyanhydride, polyorthoester, polyhydroxy acid, for example, polylactic acid, polyglycolic acid, and copolymers or blends thereof, and polyphosphazenes. Collagen can also be used, but is not as controllable as a synthetic polymer either with respect to manufacture of matrices or degradation in vivo and is therefore not preferred. These materials are all commercially available.

In some embodiments, attachment of the cells to the polymer is enhanced by coating the polymers with compounds such as basement membrane components, agar, agarose, gelatin, gum arabic, collagens types I, II, III, IV and V, fibronectin, laminin, glycosaminoglycans, mixtures thereof, and other materials known to those skilled in the art of cell culture.

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

One of the advantages of a biodegradable polymeric matrix is that angiogenic and other bioactive compounds can be incorporated directly into the matrix so that they are slowly released as the matrix degrades in vivo. As the cell-polymer structure is vascularized and the structure degrades, the cells will differentiate according to their inherent characteristics. Factors, including nutrients, growth factors, inducers of differentiation or de-differentiation (i.e., causing differentiated cells to lose characteristics of differentiation and acquire characteristics such as proliferation and more general function), products of secretion, immunomodulators, inhibitors of inflammation, regression factors, biologically active compounds which enhance or allow ingrowth of the lymphatic network or nerve fibers, hyaluronic acid, and drugs, which are known to those skilled in the art and commercially available with instructions as to what constitutes an effective amount, from suppliers such as Collaborative Research, Sigma Chemical Co., vascular growth factors such as vascular endothelial growth factor (VEGF), EGF, and HB-EGF, could be incorporated into the matrix or provided in conjunction with the matrix. Similarly, polymers containing peptides such as the attachment peptide RGD (Arg-Gly-AsP) can be synthesized for use in forming matrices.

A presently preferred polymer is polyglactin 910, developed as absorbable synthetic suture material, a 90:10 copolymer of glycolide and lactide, manufactured as Vicryl® braided absorbable suture (Ethicon, Inc., Somerville, N.J.) (Craig, P. H., Williams, J. A., Davis K. W., et al.: A Biological comparison of Polyglactin 910 and Polyglycolic Acid Synthetic Absorbable Sutures. *Surg.*, 141:1010 (1975). A commercially available surgical mesh formed of polyglycolic acid, Dexon™, can also be used.

Matrix Design

The design and construction of the scaffolding is of primary importance. The matrix should be a pliable, non-toxic, injectable porous template for vascular ingrowth. The pores should allow vascular ingrowth. These are generally interconnected pores in the range of between approximately 100 and 300 microns, i.e., having an interstitial spacing between 100 and 300 microns, although larger openings can be used. The matrix should be shaped to maximize surface area, to allow adequate diffusion of nutrients, gases and growth factors to the cells on the interior of the matrix and to allow the ingrowth of new blood vessels and connective tissue. At the present time, a porous structure that is relatively resistant to compression is preferred, although it has been demonstrated that even if one or two of the typically six sides of the matrix are compressed, that the matrix is still effective to yield tissue growth.

Fibers (sutures or non-woven meshes) can be used as supplied by the manufacturer. Other shapes can be fabricated using one of the following methods:

Solvent Casting. A solution of polymer in an appropriate solvent, such as methylene chloride, is cast on a fibrous pattern relief structure. After solvent evaporation, a thin film is obtained.

Compression Molding. Polymer is pressed (30,000 psi) into an appropriate pattern.

Filament Drawing. Filaments are drawn from the molten polymer.

Meshing. A mesh is formed by compressing fibers into a felt-like material.

At the present time, a mesh-like structure formed of fibers which may be round, scalloped, flattened, star shaped, solitary or entwined with other fibers is preferred. As discussed above, the polymeric matrix may be made flexible or rigid, depending on the desired final form, structure and function either woven, non-woven or knitted material can be used. A material such as a velour is an example of a suitable woven material. The fibers can be fused together by addition of a solvent or melting to form a more stable structure. Alternatively, high pressure jets of water onto a fibrous mat can be used to entangle the fibers to form a more rigid structure. For repair of a defect, for example, a flexible fibrous mat is cut to approximate the entire defect, then fitted to the surgically prepared defect as necessary during implantation. An advantage of using the fibrous matrices is the ease in reshaping and rearranging the structures at the time of implantation.

A sponge-like structure can also be used. The structure should be an open cell sponge, one containing voids interconnected with the surface of the structure, to allow adequate surfaces of attachment for sufficient cells to form a viable, functional implant.

Implantation of the Matrix

The matrix is implanted using standard surgical procedures, suturing edges to the tissue to be treated or adjacent materials as necessary.

This method of using a polymer as a scaffold wherein adjacent cells can migrate onto and into the polymer can be used to patch defects of urethelial associated organs such as urethra, bladder, ureters, and renal pelvis. In addition, this method can be used to entirely replace or reconstruct these structures, such as for hypospadias, where urethral reconstructive surgery is necessary, or for bladder surgery where either an augmentation is necessary for a low capacity bladder or a neobladder is needed, or for ureteral extension, replacement, or reconstruction, such as with a patient requiring additional ureteral length secondary to trauma or neoplasm. Further, this system can be used for other areas where a soft tissue replacement is needed such as in the gastrointestinal system, for example, in situations where additional intestinal tissue is needed, or in the musculo-skeletal system, such as for bone or cartilage tissue replacement secondary to congenital, neoplastic, inflammatory, or traumatic conditions.

The present invention will be further understood by reference to the following non-limiting examples.

Example 1

Urethral Reconstruction Using Biodegradable Polymer Scaffolds

The more severe forms of hypospadias are usually corrected with a vascularized preputial island graft. Patients with failed reconstruction, epispadias, or urethral strictures may not have sufficient preputial skin for repair. In these instances, several alternatives have been used, including free skin, bladder mucosa and buccal mucosa grafts. However, some of these grafts are associated with several complications, and their use is limited. The following study compares the usefulness of cell-polymer matrices and synthetic polymer matrices in the absence of seeded cells for repair of urothelial structures, especially bladder.

Materials and Methods

Urothelial cells were harvested from a small segment of the bladders of 10 New Zealand white rabbits by open surgery. The urothelial cells were plated in vitro, expanded, and tagged with 7-amino 4-chloromethylcoumarin, a fluorescent probe. Cells were resuspended in media and seeded onto biodegradable polymer scaffolds. Partial urethrectomies were performed in each rabbit through a circumcising incision. The autologous urothelial cell-polymer meshes were interposed using continuous 7-0 Vycril™ sutures to form the neourethras. Polymer meshes without urothelial cells were used in two animal as controls. The penile skin was closed over the neourethra with interrupted 5-0 Vycril™ sutures. Due to the thick, semi-solid consistency of rabbit urine, simultaneous vesicotomies were performed in order to achieve a satisfactory urinary diversion.

After vesicotomy closure, ten days after urethral reconstruction, the animals were able to void through the neourethra without complications. Retrograde urethrograms showed no evidence of stricture formation. Histologic examination of the neourethras demonstrated complete re-epithelialization of the polymer mesh sites by day 14. These findings were persistent at the four and six week time points. Fluorescent microscopy showed tagged autologous urothelial cells closely associated with the poly fibers. Urethral polymer controls showed complete re-epithelialization, by 14 days, indicating that native cells are not necessary for successful replacement of urethral defects. The polymer fibers were partially degraded by day 14 and almost totally reabsorbed by day 30.

In conclusion, biodegradable polymer meshes can be used, either alone or in combination with harvested autologous urothelial cells, for urethral reconstruction. Adequate anatomic and functional replacement can be achieved by using this technology.

Example 2

Bladder Reconstruction Using Biodegradable Polymer

Multiple anomalies of the bladder, whether congenital or acquired, require augmentation cystoplasty. In these instances, use of bowel for augmentation has been used widely. The use of gastrointestinal tissue for urologic reconstruction is associated with several complications, and their use is limited. The following study compares the usefulness of cell polymer matrices and cell-polymer matrices and synthetic polymer matrices in the absence of seeded cells for bladder reconstruction.

Urothelial cells are harvested from a small segment of the bladders of ten New Zealand white rabbits by open surgery. The urothelial cells were plated in vitro and tagged with 7-Amino 4-chloromethylcomarin, a fluorescent probe. Cells were resuspended in media and seeded onto biodegradable polymer scaffolds. Partial cystectomies were performed in each rabbit through a mid-abdominal incision. The autologous urothelial cell-polymer matrices were interposed using Vycril™ sutures to augment the small bladders. Polymer matrices without urothelial cells were used in ten additional animals as controls. Omentum was used to cover the polymer, rendering it impermeable to urine. A urethral catheter was left in place for ten days for urinary diversion.

After the catheter was removed, the animals were able to void without complications. Bladder cystograms showed an increased bladder capacity in all animals. Histological examination of the neobladders demonstrated complete re-epithelialization of the polymer mesh sites by day 14. These findings were persistent at the four and six week time points. Fluorescent microscopy showed tagged autologous urothelial cells closely associated with the polymer fibers. Bladder polymer controls showed complete re-epithelialization by 14 days, indicating that native cells are not necessary for successful bladder augmentation or reconstruction. The polymer fibers were partially degraded by day 14 and almost totally reabsorbed by day 30.

In conclusion, biodegradable polymer matrices can be used, either alone or in combination with harvested autologous urothelial cells, for bladder reconstruction. Adequate anatomic and functional replacement can be achieved by using this technology.

Example 3

Ureteral Reconstruction Using Biodegradable Polymers Scaffolds

Multiple anomalies of the ureter, whether congenital or acquired, require ureteral reconstruction. In these instances, when the ureteral tissue present cannot be used for reconstruction, other gastrointestinal tissues have been used. The use of gastrointestinal tissue, however, is associated with numerous complications when they are interposed with the urinary tract. The following study compares the usefulness of cell polymer matrices and synthetic polymer matrices in the absence of seeded cells for bladder reconstruction.

Urothelial cells were harvested from a small segment of the bladder of ten beagle dogs by open surgery. The urothelial cells were plated in vitro, expanded, and tagged with 7-amino 4-chloromethylcomarin, fluorescent probe. Cells were resuspended in media and seeded onto biodegradable polymer scaffolds. Partial ureterectomies were performed in each dog for a flank incision. The autologous urothelial cell-polymer matrices were interposed using Vicryl™ sutures to interpose these ureters. Polymer matrices without urothelial cells were used in 10 additional animals as controls. Gerota's fascia was used to cover the polymer, rendering it impermeable to urine. A ureteral catheter was left in place indwelling for ten days for urinary diversion.

After the catheter was removed, an intravenous pyelogram was performed which showed normal ureteral anatomy in each animal, without any evidence of obstruction. Histological examination of the neo-ureters demonstrated complete epithelialization of the polymer mesh sites by day 14. These findings were persistent at the 4th and 6th week time points. Fluorescent microscopy showed tagged autologous urethelial cells closely associated with the polymer fibers. Bladder polymer control showed complete re-epithelialization by 14 days, indicating that native cells are not necessary for successful ureteral reconstruction. The polymer fibers were partially degraded by day 14 and almost totally reabsorbed by day 30.

In conclusion, biodegradable polymer matrices can be used, either alone or in combination with harvested autologous urethelial cells, for ureteral reconstruction in large animals.

Although this invention has been described with reference to specific embodiments, variations and modifications of the method and means for constructing urothelial implants by implantation of polymeric matrices will be apparent to those skilled in the art. Such modifications and variations are intended to come within the scope of the appended claims.

The invention claimed is:

1. A method for correcting tissue defects in the gastrointestinal tract comprising shaping a permeable fibrous matrix to repair a tissue defect in a gastrointestinal tract, the fibrous matrix comprising a plurality of fibers formed of a biodegradable polymer, said fibrous matrix having an interstitial spacing between 100 and 300 microns; and implanting the shaped matrix at the site to be corrected, and covering the implanted shaped matrix with omentum or Gerota's fascia rendering it impermeable, wherein said interstitial spacing allows cells to grow on and into the permeable, shaped matrix.

2. A method for correcting tissue defects in urological structures comprising
   (a) shaping a permeable fibrous matrix to repair a tissue defect in a urological structure, the fibrous matrix comprising a plurality of fibers formed of a biodegradable polymer, said fibrous matrix having an interstitial spacing between 100 and 300 microns;
   (b) implanting the shaped matrix at the site to be corrected; and
   (c) covering the implanted shaped matrix of step (b) with omentum or Gerota's fascia rendering it impermeable to urine;
   wherein said interstitial spacing allows cells to grow on and into the permeable shaped matrix.

3. The method of claim 2, wherein the urological structure is a bladder.

4. The method of claim 2, wherein the urological structure is a ureter or urethra.

5. The method of claim 1 or 2, further comprising providing, with the matrix, at least one bioactive compound selected from the group consisting of nutrients, growth factors, inducers of differentiation, inducers of dedifferentiation, products of secretion, immunomodulators, inhibitors of inflammation, biologically active compounds that enhance ingrowth of the lymphatic network or nerve fibers, biologically active compounds that allow ingrowth of the lymphatic network or nerve fibers, vascular growth factors, and attachment peptides.

6. The method of claim 1 or 2, wherein the matrix is coated with at least one material selected from the group consisting of basement membrane components, agar, agarose, gelatin, gum Arabic, collagens type I, collagen type II, collagen type III, collagen type IV, collagen type V, fibronectin, laminin, and glycoaminoglycans.

7. The method of claim 1 or 2, wherein the biodegradable polymer is selected from the group consisting of poly(lactic acid-glycolic acid), polyanhydride, polyorthoester, polyhydroxy acid, polylactic acid, and polyphosphazene.

* * * * *